United States Patent
Kellenberger

[11] Patent Number: 5,931,796
[45] Date of Patent: Aug. 3, 1999

[54] LOWER EXTREMITY SUPPORT APPARATUS

[76] Inventor: David Kellenberger, P.O. Box 928, Tahoe City, Calif. 96145

[21] Appl. No.: 08/996,770

[22] Filed: Dec. 23, 1997

[51] Int. Cl.$^6$ ....................................................... A61F 5/00
[52] U.S. Cl. ............................................... 601/34; 602/23
[58] Field of Search .................................. 602/4, 10, 11, 602/23; 601/34

[56] References Cited

U.S. PATENT DOCUMENTS

| | | | |
|---|---|---|---|
| 2,664,886 | 1/1954 | Coffman | 601/34 X |
| 2,966,905 | 1/1961 | Kamenshine | 601/34 X |
| 3,502,071 | 3/1970 | Holly | 601/34 X |
| 3,739,772 | 6/1973 | Ennis | 601/34 X |
| 4,019,503 | 4/1977 | Smith | 602/4 |
| 4,336,796 | 6/1982 | Andrews et al. | 602/4 |
| 4,599,996 | 7/1986 | Seith et al. | 601/34 |
| 4,669,450 | 6/1987 | Linberg | 601/34 |
| 4,823,782 | 4/1989 | Powlan | 602/4 |
| 5,014,692 | 5/1991 | Rhoades | 601/34 X |
| 5,236,333 | 8/1993 | Barba, Jr. | 601/34 X |
| 5,253,639 | 10/1993 | Johnston | 601/34 X |
| 5,509,894 | 4/1996 | Mason et al. | 601/34 X |
| 5,582,579 | 12/1996 | Chism et al. | 601/34 X |

*Primary Examiner*—Linda C.M. Dvorak
*Attorney, Agent, or Firm*—Thomas N. Neiman

[57] ABSTRACT

A novel lower extremity support apparatus is comprised of a unit that is designed to allow the individual having a recent lower extremity operation or injury to use the apparatus to limit the loads on the surgically repaired or injured lower extremity. The apparatus also assists in controlling the range of motion for the hip, knee or ankle and provides the protection for those joints. The apparatus has an adjustable, form fitted padded member that dispersed the pressure loads across a broad surface area of the lower extremity. The padded member is connected to a rigid piece that is inserted into a standard or custom made designed lower extremity hinged brace or immobilized or an existing brace or can be attached independently. The rigid piece has an angled portion at its base portion which fits under the brace. An adjustable rope member, having a handle unit, is attached to the base of the rigid piece and is designed for allow assistance in lifting of the lower extremity. The rope member has adjustment and locking mechanism. The handle unit and the upper portion of the rigid piece have a open and closed loop connection unit for storage and convenience purposes. The lower angled portion of the rigid piece has a removable molded cover.

8 Claims, 3 Drawing Sheets

LOWER EXTREMITY SUPPORT APPARATUS

BACKGROUND OF THE INVENTION

This invention pertains to joint support devices, and in particular, to such lower extremity support apparatus that is designed to allow the user to protect, support and lift injured lower extremities before or after reconstructive surgery has been performed by allowing the apparatus to control the loads on the lower extremity, limit the range of motion, and primarily assist in the lifting and movement of the lower extremity. Therefor, this apparatus provides protection for the injured or surgically repaired lower extremity.

Many types and designs of joint and leg support and lifting devices are currently on the market. There have been many of these devices that have been patented. Examples of these devices include the U.S. Pat. No. 5,300,016 to William Marriatt for a Lower Leg Shelf With Foldable Weight Bearing Strut and Stabilizer Frame which issued on Apr. 5, 1994, the U.S. Pat. issued to Mashall Walker, No. 5,291,904 for a Dorsiflexion Assisting Device For Hemiplegics issued on Mar. 8, 1994 and the U.S. Pat. No. issued to Janice I Rhodes on Mar. 14, 1991 for an Self Manipulatable Assembly for Moving a Leg In a Cast. These devices show different approaches in supporting, protecting and lifting the leg and knee joint of an individual. What is needed is a lightweight device that an individual can easily fold and store and, at the same time, be readily available and be able to use to support the lower extremity by positioning the unit with a brace of attaching the apparatus as a separate unit. What is also needed is a device which will attach to a brace and allow and provide the user to assist in the manipulation and movement of an injured or surgically repaired lower extremity, either hip, knee or ankle.

Clearly, it is desirable for a device of this type to be very lightweight. At the same time, the device should be easy to manufacture and be produced of inexpensive material. It is the object of this invention to set forth a removable device which can be attached to a standard of custom lower extremity brace or immobilizer or as a separate unit. It is also the object of this invention to teach a lower extremity support apparatus which overcomes the limitations of previously mentioned of typical lower extremity support devices.

SUMMARY OF THE INVENTION

Particularly, it is the object of this invention to teach a lower extremity support apparatus, for use in providing a lightweight protection, support and lifting unit for individuals having a surgically repaired or injured lower extremity, comprising a padded support member for decreasing load pressures present on the lower extremity of an individual as the braced individual activity or passively tries to move an injured or surgically repaired lower extremity; a rigid piece connected to said padded support member positioned to the lower leg of an individual; said rigid piece having an angled lower portion for positioning said rigid piece beneath a portion of a brace or as a separate unit; and a rope mechanism attached to said rigid piece for permitting lifting of the injured or surgically repaired lower extremity by the use of an upper extremity.

BRIEF DESCRIPTION OF THE INVENTION

Further objects and features of this invention will become more apparent by reference to the following description taken in conjunction with the following figures, in which.

DESCRIPTION OF THE PREFERRED EMBODIMENTS

Figure 1:
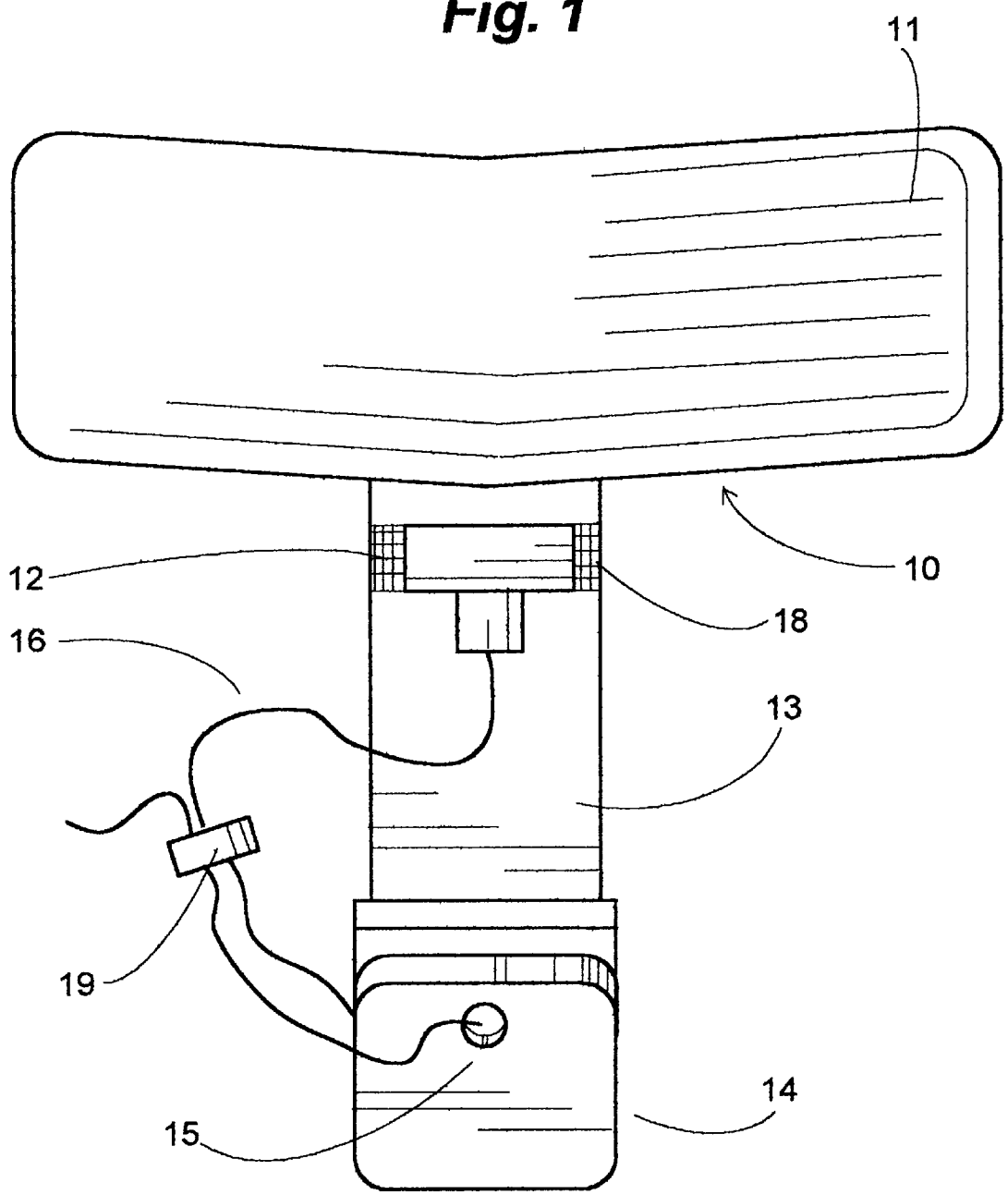
FIG. 1 is a front elevational view of the novel lower extremity support apparatus.
Figure 2:
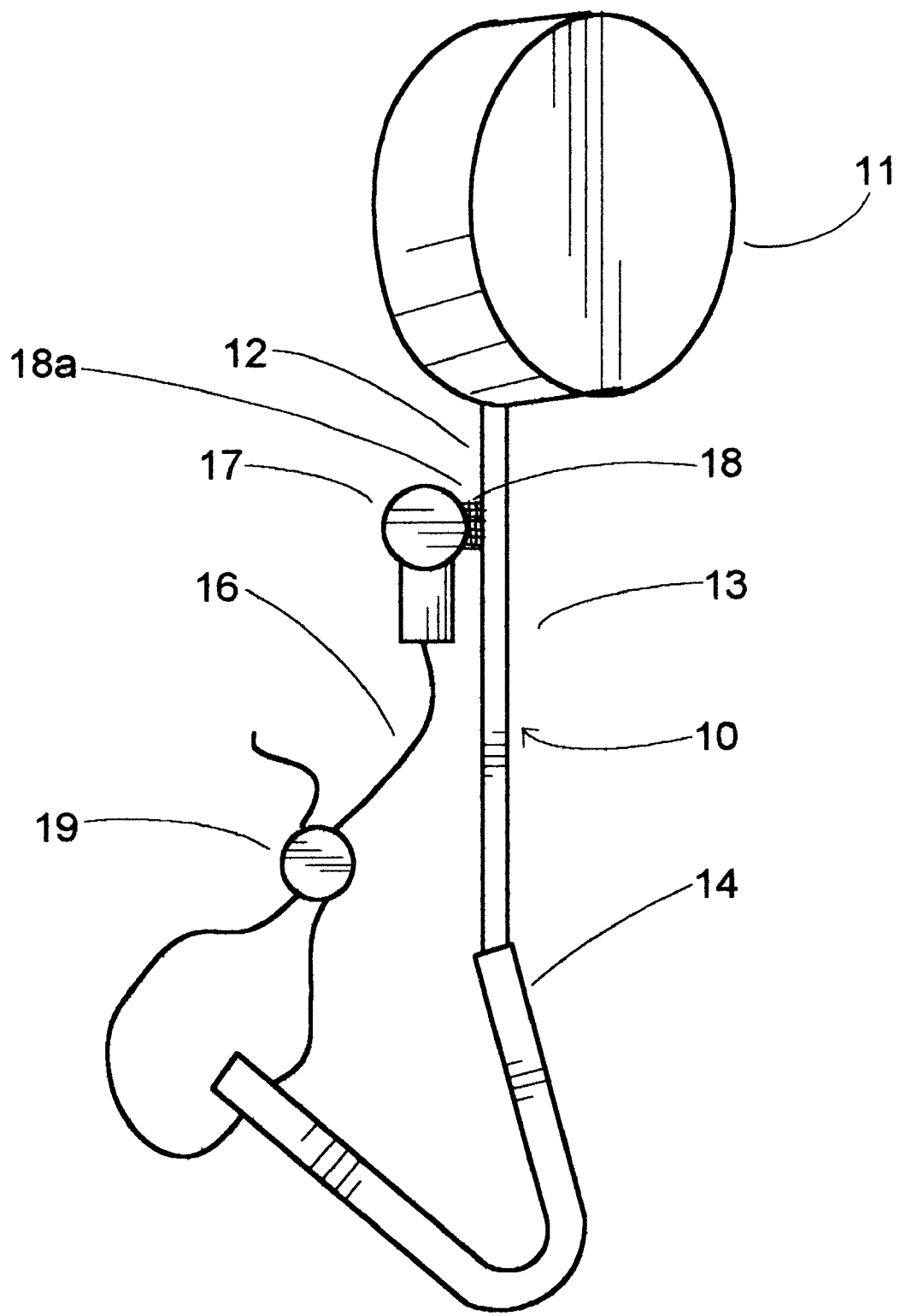
FIG. 2 is a side elevation view thereof.
Figure 3:
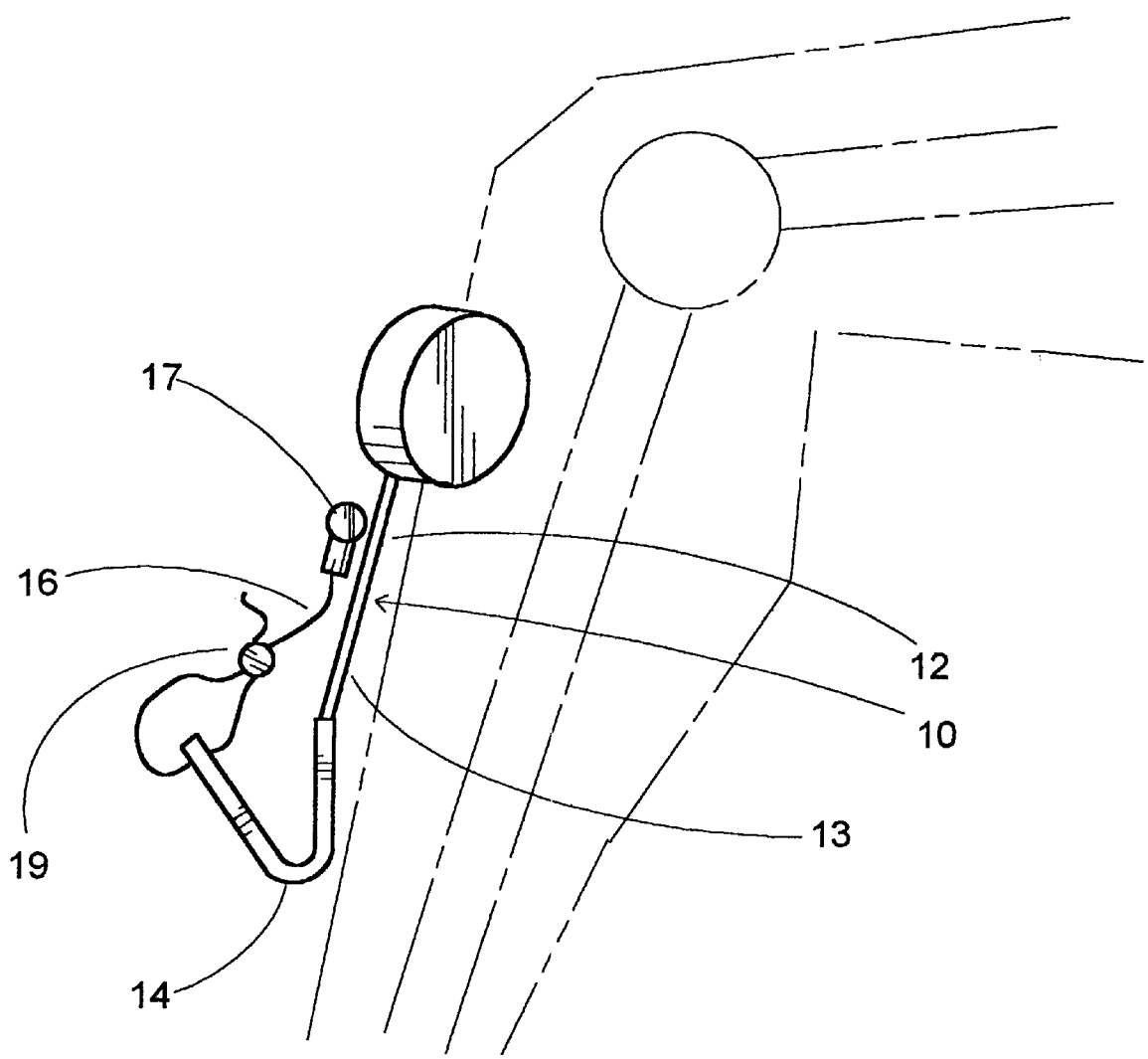
FIG. 3 is a side elevational view of the lower extremity support apparatus in position on the lower leg of an individual.

As shown in the figures, the novel lower extremity support apparatus 10 comprises a padded support member 11 which fits around the front of the leg and is adjustable to comfortably fit the leg. The cover of the padded support member can be removed for cleaning purposes. The padded support member 11 is connected to the upper end 12 of a rigid piece 13 which is designed to fit along the lower leg of an individual. The rigid piece can be constructed of metals, plastics or other suitable material. The lower portion 14 of the rigid piece 13 is a formed and molded angled unit to form a reverse C shape a portion of the rigid piece can be positioned beneath the strap of a standard or custom knee, lower extremity or immobilizing brace or with strapping as a separate unit and allow increased leverage when the device is being used. A aperture 15 is located in the lower angled portion 14 of the rigid piece 13 to receive one end of a rope assembly 16. The lower angled portion of the rigid piece has a removable cover which can be taken off for cleaning purposes. The rope assembly 16 has a handle 17 positioned at the opposite end of the rope assembly 16. Open and closed loop material fasteners 18 and 18a are attached to the handle 17 and upper end 12 of the rigid piece 13 to keep the rope assembly 16 positioned during periods of storage or when the position of the lower extremity is at rest. The rope assembly 16 also has an adjusting and locking mechanism 19 that is designed to adjust the length of the rope assembly for proper fit for each individual using the apparatus. The rope assembly 19 attached through the aperture 15 can be manufactured of any rope or plastic material which suitably fits through the aperture and can be attached to fasteners 18 and 18a. As alternate embodiment could also be a retractable rope and handle unit.

In operation, the individual desiring the support, protection and lifting assistance for the knee joint or lower leg, would position the apparatus up into position below the knee joint and along the lower leg. The lower portion of the rigid piece is positioned beneath the lower strap of a standard or custom knee or immobilizing brace or as a separate unit with attaching devices. In position, the apparatus controls and permits passive lifting of the knee joint and lower leg. It also assists as an active assisted movement of the lower extremity. The angle of the lower portion of the rigid piece increases the leverage for the individual using the apparatus. The individual uses the rope and handle assembly as necessary to lift the leg into a desired position using the hand and arm of the individual which takes the pressure off of the limb and joint and protects the surgically repaired or injured lower extremity, either hip, knee or ankle-joint. All materials that come into contact with the individual's skin can be removed and cleaned for the purpose of maintaining sanitary conditions. This apparatus is designed to allow the patient not to actively use their own lower extremity muscles thus eliminating potential dangerous forces across an injured or surgically repaired lower extremity. The design can be produced as a separate unit to be attached to a standard or custom lower extremity, knee or immobilizing brace or as a totally independent unit. It can also be designed as a prefabricated attached part of a lower extremity, knee or immobilizing brace. In either embodiment it would serve the same function in assisting the movement and positioning of an injured or surgically repaired lower extremity. The apparatus itself may be streamlined into a smaller unit which performs the same assisted functions as the above mentioned lower extremity apparatus.

While I have described my invention in connection with specific embodiments thereof, it is clearly to be understood that this is done only by way of example and not as a limitation to the scope of my invention as set forth in the objects thereof and in the appended claims.

I claim:

1. A lower extremity support apparatus, for use in providing a lightweight protection, support and lifting unit for individuals having a surgically repaired or injured lower extremity in order to remove and displace forces about the knee and leg, comprising:

a padded support member for decreasing load pressure present on the lower extremity of an individual as the braced individual actively or passively tries to move an injured or surgically repaired lower extremity while permitting the knee joint to be positioned in any predetermined position;

a rigid piece connected to said padded support member sized and configured to be positioned against the lower leg of the individual;

said rigid piece having an angled lower portion for positioning said rigid piece beneath a brace or as an separate unit;

said angled lower portion of said rigid piece comprising a reverse C shaped area designed for positioning said padded support member at a location below said knee joint of the individual on the front portion of said lower extremity; and a rope mechanism attached to said rigid piece for permitting lifting of the injured or surgically repaired lower extremity by use of an upper extremity and only for the period of time that the upper extremity is used to remove and displace the forces on the lower extremities.

2. A lower extremity support apparatus, according to claim 1, wherein:

said padded support means comprises a universal device for fitting the front portion of the individual's lower extremity below said knee joint.

3. A lower extremity support apparatus, according to claim 1, wherein:

said padded support apparatus having a removable cover means for providing a washable surface.

4. A lower extremity support apparatus, according to claim 1, wherein:

said rigid piece comprises an approximately flat plate that is sized to be positioned against the front lower portion of the individual's leg and allow the bending or movement of said knee joint of the individual.

5. A lower extremity support apparatus, according to claim 1, wherein:

said angled portion of said rigid piece having an aperture positioned therein for receiving said rope mechanism.

6. A lower extremity support apparatus, according to claim 1, wherein:

said angle portion of said rigid piece having a removable cover positioned thereon.

7. A lower extremity support apparatus, according to claim 1, wherein:

said rope mechanism having a handle means for providing a lifting mechanism to support the movement of the individual's lower extremity when desired.

8. A lower extremity support apparatus, according to claim 7, wherein:

said handle means having means for connecting said handle means to said rigid piece for storage purposes; and said connecting means comprises the use of open and closed loop fabric connection materials.

* * * * *